US00PP35125P2

(12) United States Plant Patent
Dirr et al.

(10) Patent No.: US PP35,125 P2
(45) Date of Patent: Apr. 25, 2023

(54) ***HYDRANGEA* PLANT NAMED 'RLL-12-20'**

(50) Latin Name: *Hydrangea macrophylla*
Varietal Denomination: RLL-12-20

(71) Applicant: Premier Introductions, Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 17/894,288

(22) Filed: Aug. 24, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Cassandra Bright

(57) ABSTRACT

A new and distinct cultivar of *Hydrangea* plant named 'RLL-12-20' is disclosed, characterized by purple-red new growth of foliage color, thick leaves, pink mophead inflorescence in non-aluminum-based media and blue inflorescence in aluminum-based media, and compact, rounded to spreading growth habit. The new variety is a *Hydrangea*, typically produced as an outdoor ornamental plant.

3 Drawing Sheets

Figure 1:
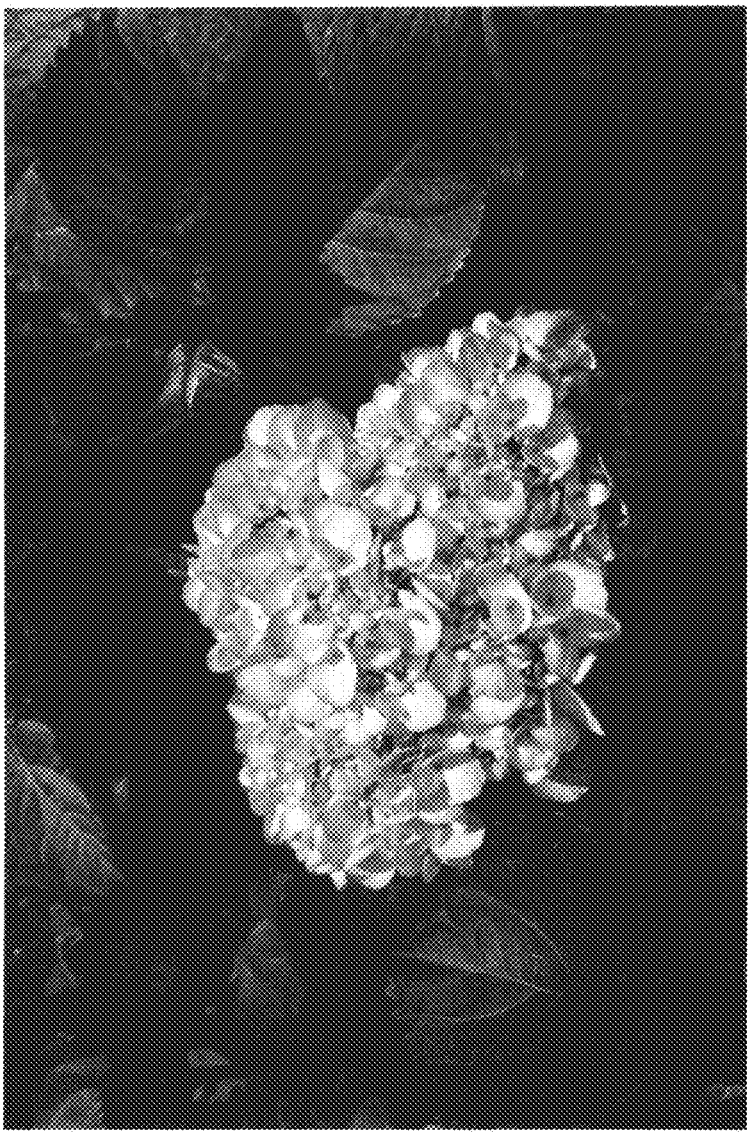

Latin name of the genus and species: *Hydrangea macrophylla.*
Variety denomination: 'RLL-12-20'.

BACKGROUND OF THE INVENTION

The present invention relates to a new and distinct cultivar of *Hydrangea macrophylla*, a member of the Hydrangeaceae family, hereinafter referred to by its cultivar name 'RLL-12-20'. This cultivar is grown primarily as an ornamental for landscape use and for use as a potted plant. The cultivar originated from an open-pollination of a red leaf *Hydrangea macrophylla* 'Lilacina' and unidentified pollen parentage in Watkinsville, Ga., in 2020, and was selected from the progeny by continued evaluation for growth habit, floral, and foliage characteristics.

'RLL-12-20' has been asexually reproduced by softwood cuttings since 2020 in Watkinsville, Ga. The characteristics of the cultivar have been stable and reproduced true to type in successive vegetative generations.

SUMMARY OF THE INVENTION

'RLL-12-20' has not been observed under all possible environmental conditions. The phenotype may vary somewhat with changes in light, temperature, soil and rainfall without, however, any variance in genotype.

The following traits have been repeatedly observed and are determined to be the unique characteristics of 'RLL-12-20.' These characteristics in combination distinguish 'RLL-12-20' as a new and distinct *Hydrangea* cultivar:

1. Thick foliage with purple-red new growth and first year stems are reddish orange.
2. Deep purplish pink mophead inflorescence in non-aluminum-based media and light purplish-blue inflorescence in aluminum-based media.
3. Compact, rounded to spreading growth habit.

PARENT COMPARISON

Plants of the new cultivar *Hydrangea* 'RLL-12-20' can be compared to the seed parent variety in most horticultural characteristics, however, plants of 'RLL-12-20' differ in the following:

1. 'RLL-12-20' is distinguished from its parent plant 'Lilacina' by its mophead inflorescence. 'Lilacina' is a lacecap.
2. The red new growth on 'Lilacina' is not as purple-red and turns green quicker than 'RLL12-20'.
3. The foliage on 'RLL-12-20' is thicker than the foliage on 'Lilacina'.
4. 'RLL-12-20' is compact compared to Red Leaf *Hydrangea macrophylla* 'Lilacina'.

COMMERCIAL COMPARISON

Plants of the new cultivar *Hydrangea* 'RLL-12-20' can be compared to the commercial variety *Hydrangea macrophylla* 'H2002', U.S. Plant Pat. No. 26,657. Plants of 'RLL-12-20' are similar to plants of 'H2002' in some horticultural characteristics, however, plants of 'RLL-12-20' differ in the following:

1. 'RLL-12-20' has deep purple Summer foliage; this comparator has some bronze coloration to the foliage, mainly in the Spring.
2. This comparator has a rose colored picotee flower; 'RLL-12-20' has either deep purplish pink inflorescences in non-aluminum-based media or light purplish-blue inflorescences in aluminum-based media.
3. The new variety has been observed to grow stronger in the environmental conditions of the South Eastern United States.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea.*

FIG. 1: shows a two-year-old 'RLL-12-20' in flower with some of the purple-red new growth.

Figure 2:
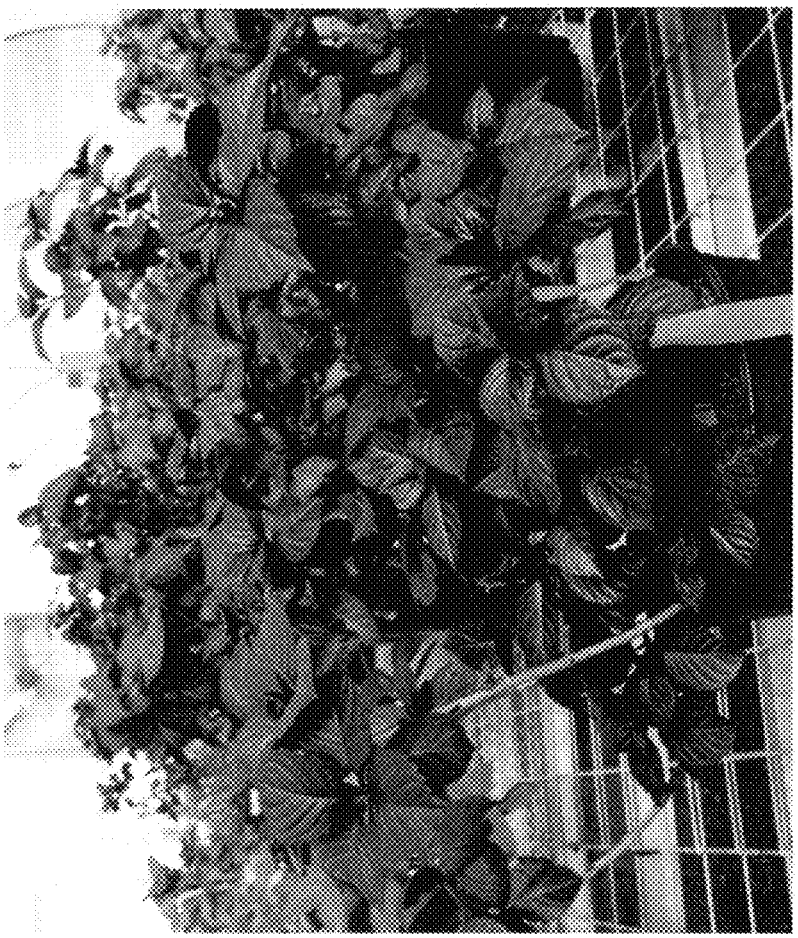

FIG. 2: shows a two-year-old 'RLL-12-20' with purple-red foliage.

Figure 3:
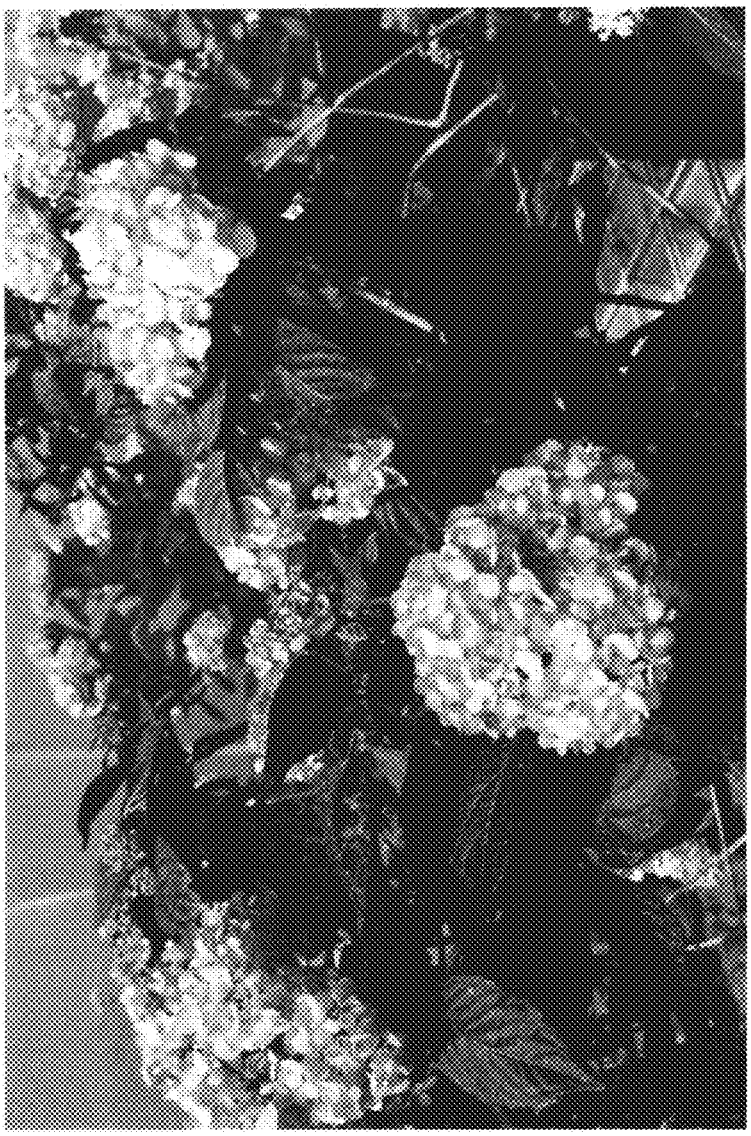

FIG. 3: shows a two-year-old 'RLL-12-20' with purple-red foliage and mophead inflorescences.

DETAILED BOTANICAL DESCRIPTION

In the following description, color references are made to The Royal Horticultural Society Colour Chart, 2015 Edition, except where general terms of ordinary dictionary significance are used. Plants used for the description were grown in 23.03 L containers under 50% shade under outdoor conditions in a nursery in Watkinsville, Ga. Plants were about two years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 60 grams of aluminum sulphate and a pH of 5.3. Aluminum only affects flower including sepal, petal, pistil and stamen colors. Therefore, colors with and without aluminum are only specified for floral parts.

Botanical classification: *Hydrangea macrophylla* 'RLL-12-20'.

PROPAGATION

Typical method: Vegetatively by stem cuttings.

Root initiation: Approximately 14 days at 32° C.

Time to produce rooted cutting: About 3 months at 32° C. during summer.

Time to produce a finished crop: In a 11.4 L container potted with a 0.041 L liner pot, about 9 months.

Roots: Root description: numerous, fine, fibrous and well-branched. Color: RHS White N155A.

PLANT

Plant type: Rounded, compact and spreading deciduous shrub.

Height: 91 cm.

Plant spread: 121 cm.

Age of plant described: Approximately 2 years.

Branching characteristics: Freely-branching. Pinching enhances branching.

*Number of lateral branches.*—About 8 per plant.

First year stems:

*Length.*—33 cm.
*Width.*—4 mm.
*Color.*—RHS Reddish Orange 174B.
*Shape.*—Round.
*Strength.*—Flexible.
*Texture.*—Smooth.

Second year stems:

*Length.*—88 cm.
*Width.*—6 mm or more.
*Color.*—RHS Brown N199D.
*Shape.*—Round.
*Strength.*—Easily broken.
*Texture.*—Woody. Exfoliation begins on second year and older stems, flaky and stringy, the color is RHS Yellow 161A.

Vegetative buds:

*Arrangement.*—Opposite.
*Shape.*—Ovoid.
*Length.*—2 mm.
*Width.*—1 mm.
*Color.*—RHS Red 184A.

FOLIAGE

Leaf:

*Arrangement.*—Opposite, simple.
*Shape.*—Ovate.
*Length.*—17 cm.
*Width.*—14 cm.
*Apex.*—Acuminate.
*Base.*—Cuneate.
*Margin.*—Serrate.
*Strength.*—Durable.
*Texture of top surface.*—Glabrous.
*Texture of bottom surface.*—Glaucescent.
*Color.*—Young foliage upper side: RHS Red N186C. Young foliage under side: RHS Brown 200C. Mature foliage upper side: RHS Yellow-Green 147A. Mature foliage, under side: RHS Yellow-Green 146C. Summer foliage upper side: RHS Red 187A. Summer foliage, under side: RHS Red N186C. Fall foliage: Can be RHS Red-Purple N77A, Yellow-Green 143A, or any combination of these colors.

Venation:

*Type.*—Pinnate.
*Color.*—Young, upper side: RHS Yellow-Green 143C. Young, under side: RHS Yellow-Green 146C with some Red 59A. Mature, upper side: RHS Yellow-Green 143C. Mature, under side: RHS Yellow-Green 146C with some Red 59A.

Petiole:

*Length.*—2 cm.
*Width.*—2.5 mm.
*Color.*—Upper side: RHS Red 59A. Under side: RHS Red 59A.
*Texture.*—Smooth, glabrous. Petiole is grooved on upper side, and crescent-shaped in cross section.

INFLORESCENCE

Natural flowering season: Early to mid-summer. The inflorescence is effective for about 8 weeks.

Inflorescence type: Mophead.

*Height.*—7 cm.
*Diameter.*—13 cm.

Fragrance: None.

Bud:

*Bud length.*—6 mm.
*Bud diameter.*—4 mm.
*Bud shape.*—Round.
*Bud color.*—Prior to opening: RHS Yellow-Green 145B-C. When opening, with aluminum: RHS Purple N82B. When opening, without aluminum: RHS Purplish Red 63C.

Sterile florets:

*Flowers per inflorescence.*—About 458.
*Shape.*—Ovoid.
*Tip.*—Obtuse.
*Base.*—Acute.
*Margin.*—Entire.
*Diameter.*—3 mm.

Sepals:
*Number per flower.*—4.
*Length.*—2 cm.
*Width.*—Less than 1 cm.
*Texture.*—Upper side: Smooth. Under side: Smooth.
*Color.*—
*At maturity, with aluminum.*—Upper side: RHS Blue 106B. Under side: RHS Purplish Blue 97B.
*At maturity, without aluminum.*—Upper side: RHS Purplish Pink 73A. Under side: RHS Purplish Pink 73D.
*Aged sepals, with aluminum.*—Upper side: RHS Light Purple 85C. Under side: RHS Light Purple 85D.
*Aged sepals, without aluminum.*—Upper side: RHS White 155B with a hint of Purplish Pink 62D. Under side: RHS White I55C with a hint of Purplish Pink 62D.

Fertile flowers:
*Flowers per inflorescence.*—About 47.

Petals:
*Number per flower.*—5.
*Shape.*—Ovate.
*Tip.*—Acuminate.
*Base.*—Truncate.
*Margin.*—Entire.
*Length.*—3 mm.
*Width.*—1.5 mm.
*Texture.*—Smooth, no pubescence.
*Color.*—With aluminum, upper side: RHS Purplish Blue 96C. With aluminum, under side: RHS Purplish Blue 97B. Without aluminum, upper side: RHS Purplish Pink 68C. Without aluminum, under side: RHS Purplish Pink 69B.
*Sepal color.*—With aluminum, upper side: RHS Purplish Blue 96C. With aluminum, under side: RHS Purplish Blue 96C. Without aluminum, upper side: RHS Purplish Pink 63C. Without aluminum, under side: RHS Purplish Pink 63C.

Peduncle:
*Length.*—4.5 cm.
*Diameter.*—4 mm.
*Angle.*—Upright.
*Strength.*—Moderately strong and flexible.
*Color.*—RHS Yellow-Green 144A.

Pedicel:
*Length.*—1.2 cm.
*Diameter.*—1 mm.
*Angle.*—45°.
*Strength.*—Moderately strong and flexible.
*Texture.*—Smooth.
*Color.*—With aluminum: RHS Purplish Blue 98D. Without aluminum: RHS Yellow-Green 145B.

REPRODUCTIVE ORGANS

Stamens:
*Number.*—4 to 5 per flower.
*Filament length.*—3 mm.
*Filament color.*—With aluminum: RHS Purplish Blue 100B. Without aluminum: RHS Purplish Red 62C.

Anthers:
*Length.*—About 1 mm.
*Width.*—0.5 mm.
*Color.*—With aluminum: RHS Purplish Blue 100B. Without aluminum: RHS Purplish Red 62D.
*Pollen amount.*—Moderate.
*Pollen color.*—RHS Yellow-White 155D.

Pistil:
*Number.*—1.
*Length.*—3 mm.
*Width.*—1.5 mm.
*Color.*—With aluminum: RHS Purplish Blue 100B. Without aluminum: RHS Purplish Red 63B.

Stigma:
*Number.*—2 or 3.
*Shape.*—Round.
*Color.*—With aluminum: RHS Purplish Blue 100B. Without aluminum: RHS Purplish Red 62B.
*Style length.*—2 mm.
*Style shape.*—Tubular.
*Style color.*—With aluminum: RHS Purplish Blue 100A. Without aluminum: RHS Purple 85D.

OTHER CHARACTERISTICS

Fruit:
*Number.*—Varies widely.
*Shape.*—Ovoid.
*Length.*—3 mm.
*Width.*—2 mm.
*Color.*—During ripening: RHS Purplish Pink 54B. At maturity: Near RHS Brown 200C.

Seeds:
*Number.*—About 50 seeds per capsule.
*Shape.*—Round.
*Length.*—0.5 mm.
*Width.*—0.5 mm.
*Color.*—Near RHS Brown 199B.

Disease resistance: Susceptibility or resistance to diseases beyond that typically found in other *Hydrangea macrophylla* plants has not been observed.

Drought tolerance and cold tolerance: USDA Hardiness Zone Map (2012): Zones 5-9.

What is claimed is:

1. A new and distinct cultivar of *Hydrangea* plant named 'RLL-12-20' as herein illustrated and described.

* * * * *